US009472224B2

(12) United States Patent
Macken et al.

(10) Patent No.: US 9,472,224 B2
(45) Date of Patent: Oct. 18, 2016

(54) ELECTRICALLY REMOVABLE HEATER FOR A THERMALLY ACTUATABLE THERMAL ASPERITY SENSOR

(71) Applicant: Seagate Technology LLC, Cupertino, CA (US)

(72) Inventors: Declan Macken, Prior Lake, MN (US); Erik Hutchinson, Eden Prairie, MN (US); Brian William Karr, Savage, MN (US)

(73) Assignee: SEAGATE TECHNOLOGY LLC, Cupertino, CA (US)

( * ) Notice: Subject to any disclaimer, the term of this patent is extended or adjusted under 35 U.S.C. 154(b) by 0 days.

(21) Appl. No.: 14/097,412

(22) Filed: Dec. 5, 2013

(65) Prior Publication Data

US 2015/0162038 A1 Jun. 11, 2015

(51) Int. Cl.

| | |
|---|---|
| ***G11B 21/02*** | (2006.01) |
| ***G11B 5/60*** | (2006.01) |
| ***G01N 25/72*** | (2006.01) |
| ***G01K 13/00*** | (2006.01) |

(52) U.S. Cl.

CPC ............... *G11B 5/607* (2013.01); *G01K 13/00* (2013.01); *G01N 25/72* (2013.01); *G11B 5/6076* (2013.01)

(58) Field of Classification Search

CPC .............. G11B 2005/0021; G11B 2005/0005; G11B 5/6005; G11B 5/59635; G11B 5/54; G11B 5/012; G11B 5/314; G11B 11/10554; G11B 5/3903; B28Y 10/00

USPC .................. 360/75, 31, 55, 59, 125.31, 128; 369/13.13, 13.33, 13.32, 13.26

See application file for complete search history.

(56) References Cited

U.S. PATENT DOCUMENTS

| | | | | |
|---|---|---|---|---|
| 5,867,461 | A | 2/1999 | Baas | |
| 6,233,127 | B1 | 5/2001 | Shimazawa | |
| 6,483,657 | B1 | 11/2002 | Fioravanti et al. | |
| 6,754,015 | B2 * | 6/2004 | Erden et al. | 360/25 |
| 7,009,820 | B1 | 3/2006 | Hogg | |
| 8,139,310 | B1 | 3/2012 | Hogg | |
| 8,169,751 | B2 * | 5/2012 | Albrecht | G11B 5/40 360/234.5 |
| 8,351,157 | B2 * | 1/2013 | Nishioka et al. | 360/125.31 |
| 8,477,456 | B2 | 7/2013 | Kautzky et al. | |
| 8,730,607 | B1 | 5/2014 | Garzon et al. | |
| 8,804,272 | B1 * | 8/2014 | Dakroub et al. | 360/75 |
| 8,810,952 | B2 * | 8/2014 | Johnson et al. | 360/75 |
| 2003/0043491 | A1 | 3/2003 | Ridderring | |

(Continued)

OTHER PUBLICATIONS

Office Action dated Nov. 23, 2015 from U.S. Appl. No. 14/865,341, 13 pages.

(Continued)

*Primary Examiner* — Nabil Hindi

(74) *Attorney, Agent, or Firm* — Hollingsworth Davis, LLC

(57) ABSTRACT

An apparatus comprising a writer, a reader, and a sensor configured to at least sense thermal asperities of a magnetic storage medium. The apparatus includes a writer heater configured to thermally actuate the writer, a reader heater configured to thermally actuate the reader, and a sensor heater configured to thermally actuate the sensor. The thermally actuated sensor is configured to detect thermal asperities arising from the magnetic storage medium during a topographical survey of the medium. The sensor heater is configured to be rendered inoperable subsequent to the survey in response to receiving a predetermined signal while the writer and the reader heaters remain operable.

21 Claims, 9 Drawing Sheets

(56) References Cited

U.S. PATENT DOCUMENTS

2005/0002303 A1 1/2005 Kwon et al.
2005/0162785 A1 7/2005 Granstrom et al.
2007/0097557 A1 5/2007 Seagle
2007/0201155 A1* 8/2007 Iwase .............................. 360/31
2008/0019032 A1 1/2008 Hayakawa et al.
2009/0168214 A1 7/2009 Araki et al.
2009/0310246 A1* 12/2009 Takahashi ....................... 360/75
2010/0091401 A1 4/2010 Ohwe
2012/0120519 A1 5/2012 Kunkel et al.
2014/0119164 A1 5/2014 Wilson et al.

OTHER PUBLICATIONS

File History for U.S. Appl. No. 14/865,341.

* cited by examiner

ELECTRICALLY REMOVABLE HEATER FOR A THERMALLY ACTUATABLE THERMAL ASPERITY SENSOR

SUMMARY

Various embodiments of the disclosure are directed to an apparatus comprising a transducer configured to interact with a magnetic storage medium, a sensor at the transducer and configured to at least sense thermal asperities of the medium, and a sensor heater configured to thermally actuate the sensor. In some embodiments, the sensor heater is electrically removable, such that it can be rendered electrically inoperable after use.

Certain embodiments of the disclosure are directed to an apparatus comprising a writer, a reader, and a sensor configured to at least sense thermal asperities of a magnetic storage medium. The apparatus includes a writer heater configured to thermally actuate the writer, a reader heater configured to thermally actuate the reader, and a sensor heater configured to thermally actuate the sensor. The sensor heater is electrically coupled between the writer and reader heaters, and is configured to receive an electrical current load greater than that of the writer and reader heaters. The sensor heater is configured to be rendered inoperable in response to receiving a predetermined signal while the writer and the reader heaters remain operable.

Embodiments are directed to a method comprising thermally actuating a sensor of a slider using a sensor heater, the sensor configured to at least sense thermal asperities of a magnetic storage medium. The method also comprises scanning a magnetic storage medium for thermal asperities using the thermally actuated sensor, and rendering the sensor heater inoperable after use in response to the sensor heater receiving a predetermined signal.

These and other features and aspects of various embodiments may be understood in view of the following detailed discussion and accompanying drawings.

DETAILED DESCRIPTION

Figure 1:
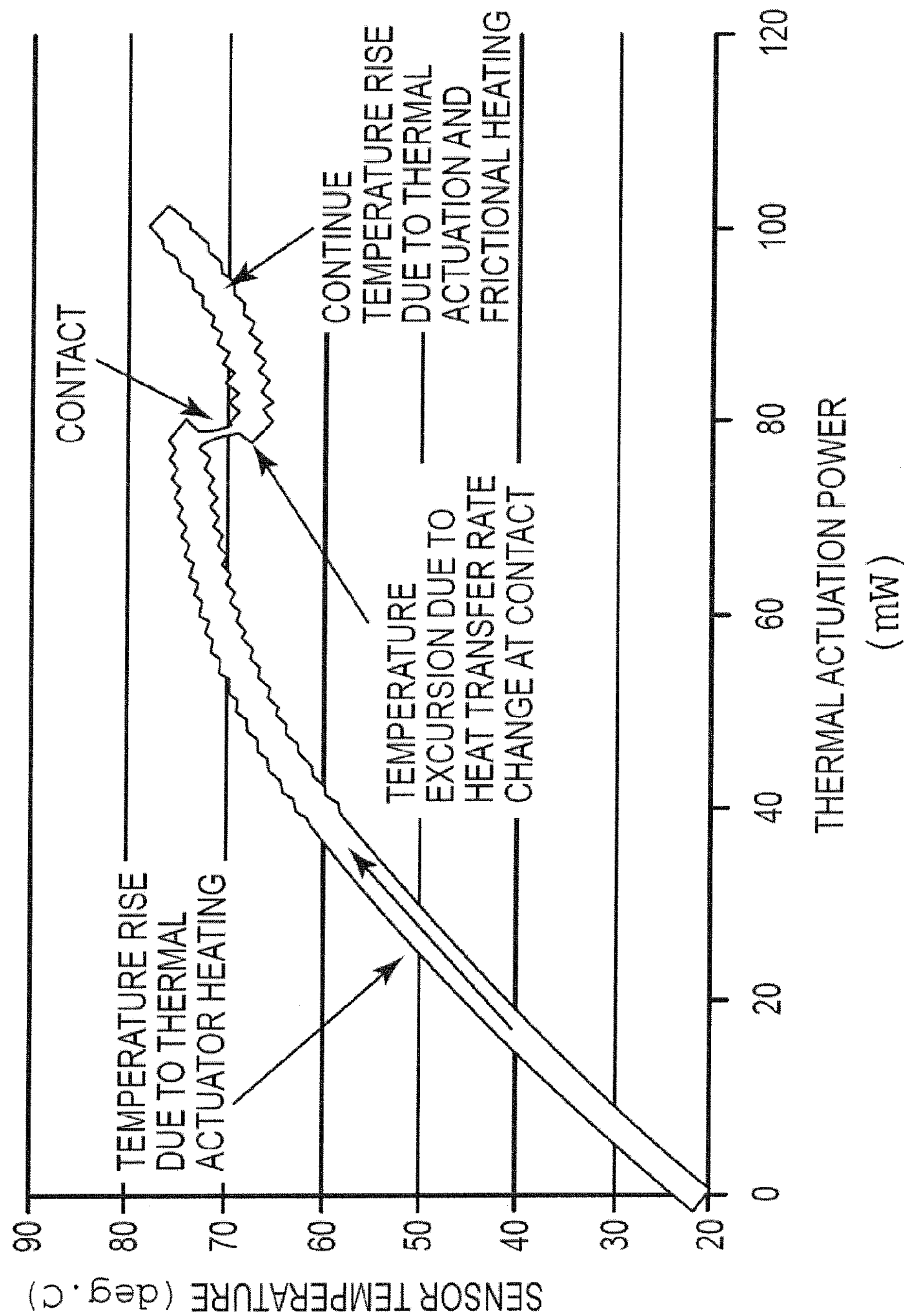
FIG. 1 is a representative temperature profile at a contact point of a transducer before, during, and after contact with a thermal asperity.

Data storage systems commonly include one or more magnetic heads having a transducer configured to write and read information to and from a magnetic storage medium. A relatively small distance or spacing is maintained between the transducer and the magnetic storage medium. This distance or spacing is generally known as the "fly height" or "head-medium spacing." The quantity of data that can be stored (e.g., written) on the magnetic storage medium, generally known as the "areal density," can be increased by reducing the fly height during the writing process. Also, by decreasing the fly height, the transducer is able to more accurately write and read data to and from the magnetic storage medium. Reducing the fly height can also enable a more accurate surveying (e.g., mapping) of the topography of the surface of the magnetic storage medium, such as identifying the locations of asperities, voids, and other features (e.g., abnormalities) on the surface of the magnetic storage medium. However, overly reducing the fly height can lead to contact between the transducer and the magnetic storage medium during read/write operations. Such contact can damage the transducer and/or the magnetic storage medium and render them unusable.

In some non-limiting representative embodiments, the magnetic head (e.g., the transducer) can be used for surveying (e.g., mapping) the topography of the surface of a "new magnetic storage medium" prior to a first write operation. As used herein, the term "new magnetic storage medium" implies a magnetic storage medium that has not been previously used and, as such, does not contain any data. In some embodiments, the topographical information can be used during the write operation to prevent or minimize loss of data by avoiding the locations having asperities, voids, etc. (e.g., not storing data at those locations). In certain embodiments, the topographical information can be used to prevent or minimize damage to the reader/writer by avoiding (e.g., not reading/writing data) the locations having asperities, voids, etc. In some embodiments, this can be accomplished by controlling the fly height during the read/write operations. For instance, the fly height can be controlled to avoid the asperities, voids, etc., by manipulating the amount of thermal energy supplied by the heat source (e.g., the reader/writer heater).

Described herein are non-limiting representative embodiments of apparatuses and methods of mapping the topography of the surface of the magnetic storage medium and optionally detecting head-medium contact during read/write operations. In various embodiments, the apparatus includes a transducer having a sensor and a sensor heater thermally coupled to the transducer. According to various embodiments, the sensor is configured to sense thermal asperities of the magnetic storage medium. In some embodiments, the sensor is configured to sense thermal asperities of the magnetic storage medium and contact between the transducer and a surface of the magnetic storage medium. In certain embodiments, the apparatus includes a transducer having a contact pad, a thermal asperity/contact sensor adjacent to the contact pad, and a sensor heater thermally coupled to the transducer.

In general, an apparatus of the disclosure includes one or more thermally actuatable sensors. In some embodiments, one or more of the sensors are configured to sense for thermal asperities. In certain embodiments, one or more of the sensors are implemented as contact sensors configured for sensing thermal asperities and sensing head-medium contact. For purposes of convenience and not of limitation, the term "sensor" in the following text refers to any sensor capable of sensing for thermal asperities, exclusive of or in addition to sensing for contact between a structure supporting the sensor (e.g., a slider) and a surface of a magnetic storage medium, unless otherwise specified.

In some embodiments, one or more sensors are implemented as thermal sensors, such as resistance thermal sensors, thermistors, and thermocouples, for example. Certain embodiments disclosed herein are directed to sensors having a temperature coefficient of resistance (referred to herein as TCR sensors), it being understood that other forms and/or means of sensing temperature are considered as being within the metes and bounds of the instant disclosure. Some of the TCR sensors described herein are referred to as Dual-ended Thermal Coefficient of Resistance (DeTCR) sensors. Another example of a TCR sensor is a ground-split (GS) temperature coefficient of resistance sensor, in which one end of the GSTCR is coupled to ground and the other is coupled to a bias source.

In some embodiments, one or more sensors (e.g., TCR, DeTCR, GSTCR) are configured to indicate a temperature by measuring a resistance across the sensor. In certain embodiments, one or more sensors are configured to indicate a change in temperature by measuring a change in the resistance across the sensor. In some embodiments, one or more sensors are configured to indicate a rate of change in temperature by measuring a rate of change in resistance across the sensor. As will be described in further detail, the onset of transducer contact with thermal asperities and/or a surface of a magnetic storage medium will cause a change in the temperature in the vicinity of the contact point. In some embodiments, one or more sensors are located on the transducer proximate to, or at, the air bearing surface (ABS). As such, the one or more sensors are configured to detect (e.g., indicate) contact with thermal asperities and/or a surface of a magnetic storage medium by sensing the temperature and/or a change in the temperature and/or a rate of change of the temperature at, or in the proximity of, the ABS. In some embodiments, a sensor of a transducer can be configured to both sense for thermal asperities and serve as a collision arrangement (e.g., a burnisher) implemented at or near the ABS. The collision arrangement, for example, can be implemented as a structure designed to make initial contact with thermal asperities, thereby severing the asperities upon contact and protecting other components of the transducer at or near the ABS.

Some embodiments of the apparatus include one or more heat sources, each thermally coupled to and configured to heat the transducer. The one or more heat sources may be resistive heaters (e.g., resistive heating elements), each configured to generate thermal heat when electrical current flows therethrough. However, the heat sources are not limited to resistive heaters, and may include any type of heat source. The thermal energy generated by the heat sources heats the transducer such that the temperature at, and in the vicinity of, the heater becomes substantially higher than the temperature of the magnetic storage medium. This results in thermal expansion of the transducer at, and in the vicinity of, the heat source. The thermal expansion of the transducer induces movement of at least the heated portion of the transducer towards the magnetic storage medium, thus decreasing the fly height at the expanded portion of the transducer. With continued application of heat, the heated portion of the transducer will continue expanding towards the magnetic storage medium until a desired fly height (or medium contact) is reached. Accordingly, one or more sensors (e.g., TCR sensors) positioned in the vicinity of the expanding portion of the transducer can be used to sense a change in temperature as indicative of transducer fly height, contact with asperities, and contact with a surface of the magnetic storage medium. In some embodiments, the fly height can be controlled by manipulating the thermal energy generated by the heat source.

In some embodiments, the extent of the thermal asperities (e.g., the height of the thermal asperities arising from the read/write surface of the magnetic storage medium) may be greater than the necessary or desirable distance that must be maintained between the transducer and the surface of the magnetic storage medium (e.g., maintaining a desired fly height). As will be apparent, the thermal asperities can damage the transducer if the fly height is smaller (e.g., shorter) than the height of the thermal asperities. Therefore, it may be necessary or desirable to burnish the surface of the magnetic storage medium such that the height of the thermal asperities is less than at least the necessary or desired fly height. Accordingly, in certain embodiments, the transducer may be configured to burnish the surface of the magnetic storage medium. Additionally, or in the alternative, the transducer may include a burnisher at or proximate to the ABS. As described elsewhere, the thermal energy generated by a heat source in the vicinity of the transducer location used for burnishing the medium and/or in the vicinity of the burnisher can be manipulated to maintain the fly height at or below a predetermined value. As will be apparent, by maintaining the fly height at the predetermined value, the transducer and/or the burnisher can be used to "shave off" (e.g., by grinding or cutting) portions of the thermal asperities that extend above the desired fly height. As such, the thermally actuated transducer and/or the burnisher may be used to burnish the surface of the magnetic storage medium. In some embodiments, a new magnetic storage medium can be burnished before any read/write operation and/or during a topographical survey operation.

FIG. 1 is a representative temperature profile for a transducer before, during, and after contact between the transducer and a portion of the magnetic storage medium, including contact between the transducer and asperities on the transducer-facing surface of the medium. In this illustrative example, the temperature profile is represented as a steady state DC signal due to a low- or non-modulating head-medium interface. As shown, the temperature of the transducer in the vicinity of the ABS increases relative to the temperature of the magnetic storage medium. The magnetic storage medium will therefore acts as a heat sink. At the onset of contact between the transducer and asperities on the magnetic storage medium, the rate of heat transfer from the transducer to the magnetic storage medium will increase, resulting in a drop (or an excursion) in the temperature at the ABS. Thereafter, if contact between the transducer and the asperities continues, the temperature at the ABS will start to increase because of thermal energy generated by friction between the transducer and the asperities and heat from the heat source. In some embodiments, such changes or excursions in the temperature of the transducer can be used as an indication of contact between the transducer and the medium, including contact between the transducer and asperities on the medium.

In certain embodiments, one or more sensors (e.g., TCR, DeTCR, GSTCR) are positioned in the proximity of a reader and/or a writer. Actuation of the reader heater and/or the writer heater (e.g., during read and/or write operation) will cause the transducer to expand towards the magnetic storage medium. The reader and/or the writer, and the sensor positioned proximate thereto, will also move towards the magnetic storage medium. As such, the reader and the writer are considered as having been "actuated" (e.g., thermally actuated) by their respective heaters. The sensor proximate the reader and/or the writer can be used to detect head-medium contact during the read and/or write operation.

Figure 2A:
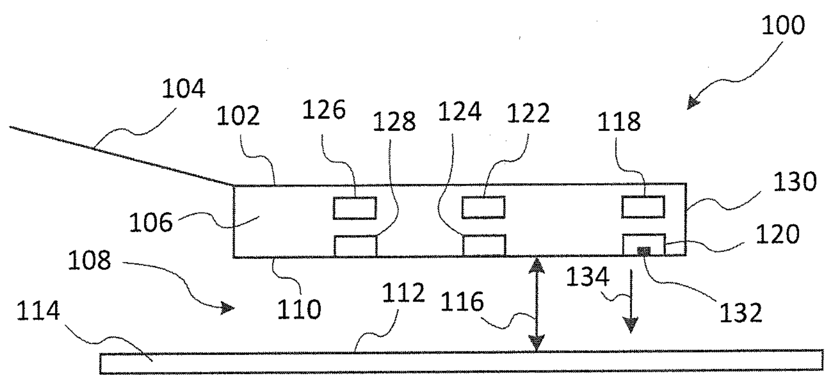
FIG. 2A is a simplified side view of a non-limiting representative embodiment of a magnetic head having a transducer incorporating a sensor, the sensor configured to at least sense thermal asperities of a magnetic storage medium in accordance with various embodiments.
Figure 2B:
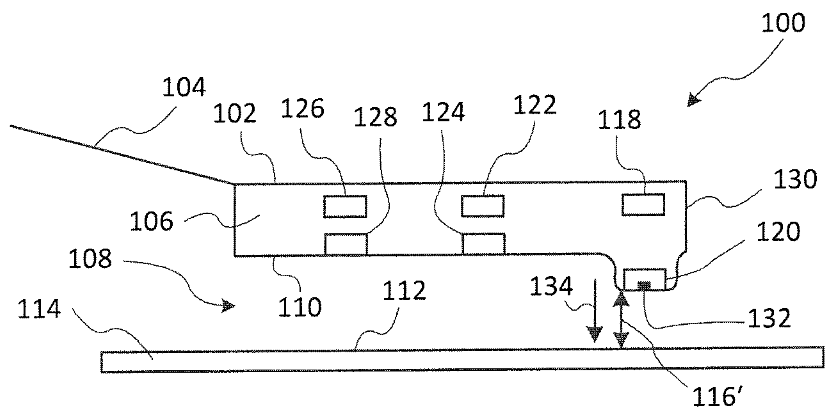
FIG. 2B illustrates the transducer of FIG. 2A prior to contact with a thermal asperity in accordance with various embodiments.
Figure 2C:
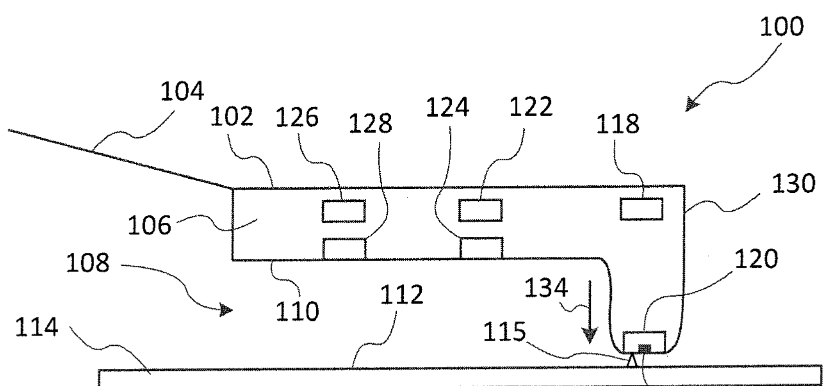
FIG. 2C shows the transducer of FIG. 2B at the onset of contact with a thermal asperity in accordance with various embodiments.

FIGS. 2A-2C are simplified side views of a non-limiting representative embodiment of a magnetic head 100 having a slider 102 supported by suspension 104. The slider 102 supports a transducer 106 having a medium facing surface 110, also referred to as an air bearing surface (ABS). An air bearing 108 is defined between the ABS 110 and a transducer facing surface 112 of a magnetic storage medium 114. As previously discussed, the distance between the ABS 110 and medium surface 112 is generally known as a fly height 116 of the transducer 106. In some embodiments, the transducer 106 includes a sensor heater 118 in proximity of a sensor 120, a writer heater 122 in proximity of a writer 124, and a reader heater 126 in proximity of a reader 128. The sensor 120 (e.g., TCR, DeTCR, GSTCR), the writer 124 and the reader 128 are positioned at, or proximate to, the ABS 110. The heaters (e.g., heat sources) 118, 122 and 126 are thermally coupled to the transducer 106. Electrical activation of the one or more of the heaters 118, 122 and 126 thermally actuates the corresponding sensor 120, writer 124 and reader 128. The thermally actuated sensor 120, writer 124 and reader 128 move towards the magnetic storage medium 114, thereby decreasing the distance therebetween. In other words, thermal actuation of the sensor 120, writer 124 and reader 128 decreases the fly height 116 at the corresponding locations of the transducer 106.

In FIGS. 2A-2C, the sensor heater 118 and the sensor 120 are shown as being located proximate a trailing edge 130 of the transducer 106. However, such positioning at the trailing edge 130 is not an absolute requirement. As described elsewhere, one or more heat sources (e.g., sensor heaters 118) and/or one or more sensors (e.g., sensors 120) may be positioned at one or more locations of the transducer 106.

FIG. 2A depicts representative positioning of the transducer 106 relative to the magnetic storage medium 114 while the sensor heater 118 is in a quiescent state. For discussion purposes, a contact point 132 is defined as that location on the sensor 120 whereat there is contact between the transducer 106 and the magnetic storage medium 114. Actuation of the heat source (e.g., sensor heater 118) in the vicinity of the sensor 120, thermally actuates the sensor 120 towards the magnetic storage medium 114. As depicted by the directional arrow 134, the contact point 132 (e.g., the sensor 120), will move towards the magnetic storage medium 114. As such, the distance between the thermally actuated sensor 120 and the magnetic storage medium 114 will decrease. In other words, the fly height 116 will decrease.

In the representative embodiment described herein, FIGS. 2A and 2B illustrate the fly height progressively decreasing from the distance depicted as 116 in FIG. 2A to the distance depicted as 116' in FIG. 2B. With continued heating, the distance between the thermally actuated sensor 120 and the magnetic storage medium 114 will continue to decrease until a predetermined fly height is reached for purposes of scanning the medium surface for thermal asperities, as illustrated in FIG. 2C. FIG. 2C shows contact between the sensor 120 and a thermal asperity 115 arising from the surface 112 of the magnetic storage medium 114. Asperity contact at the contact point 132 is detected by the sensor 120, and the corresponding location of the detected asperity on the medium surface 112 can be recorded. The transducer 106 can be repositioned to similarly identify and record other locations of asperity contact on the surface 112 of the magnetic storage medium 114. In this manner, the topography of the surface 112 of the magnetic storage medium 114 can be mapped by repeatedly repositioning the transducer 106, actuating the heat source corresponding to the sensor 120 (e.g., the sensor heater 118), detecting asperity contact events, and recording the location thereof. After the entire surface 112 of the magnetic storage medium 114 has been scanned, the heat source (e.g., sensor heater 118) can be rendered inoperable, and the sensor 120 associated with the inoperable heater 118 can be either be invalidated for future use or, alternatively, be used to detect head-medium contact during read/write operations. It is noted that a contact sensor can be situated proximate the writer 124 and/or the reader 128, and that these contact sensor(s) can be used for head-medium contact detection after the sensor heater 118 has been rendered inoperable.

It should be apparent that although FIGS. 2A-2C show only one sensor heater 118 and only one sensor 120, additional or alternative embodiments of transducer 106 can include a multiplicity of sensor heaters and/or a multiplicity of sensors. In such embodiments, the multiplicity of sensor heaters and sensors can be placed at different locations on the transducer.

Figure 3:
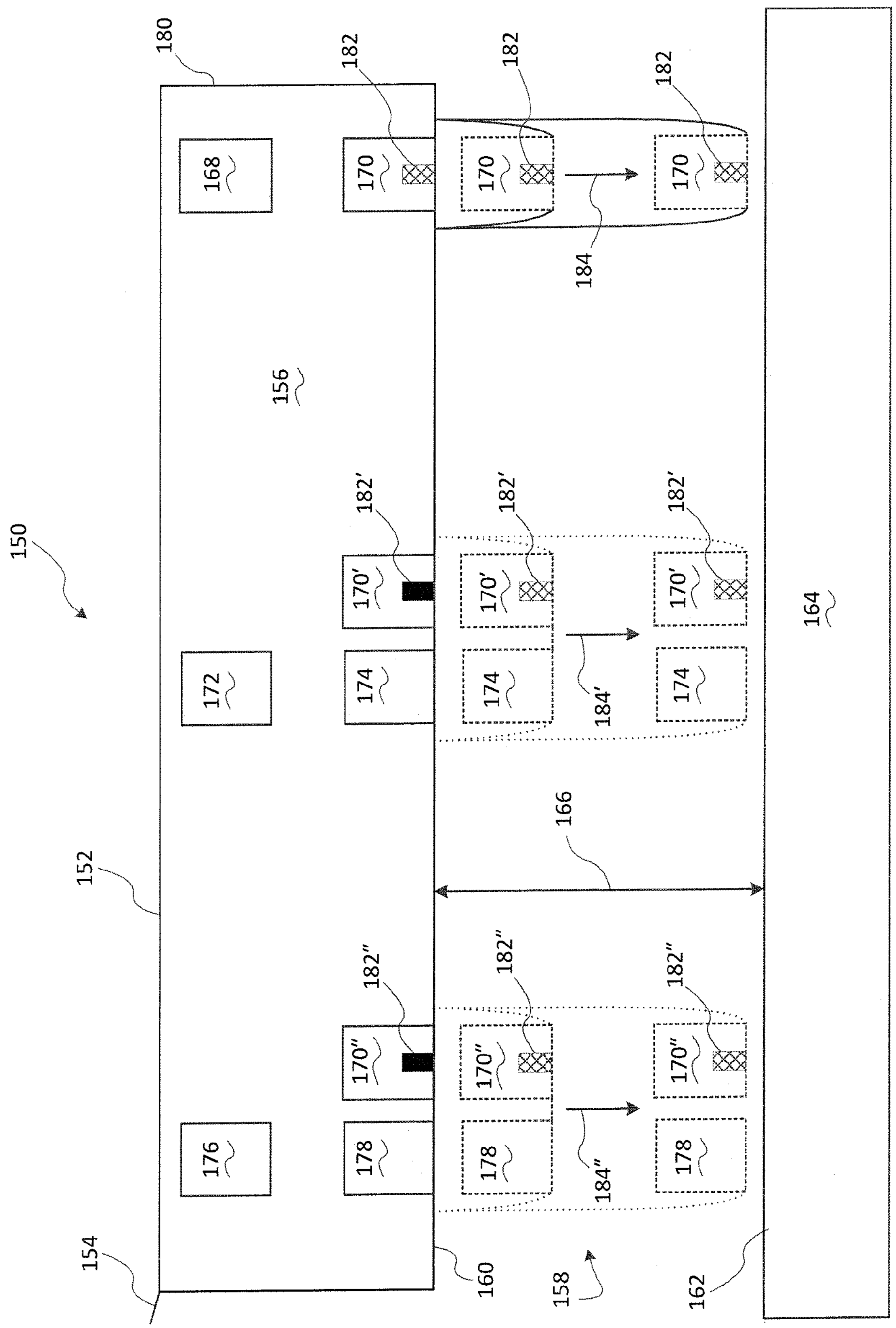
FIG. 3 is a side view of a transducer thermally actuated by a heat source in accordance with various embodiments.

FIG. 3 illustrates a non-limiting representative embodiment of a magnetic recording head 150 having a slider 152 supported by suspension 154. The slider 152 supports a transducer 156. An air bearing 158 is shown separating a medium facing surface 160 (ABS) of the transducer 156 from a transducer facing surface 162 of a magnetic storage medium 164. The distance between the ABS 160 and medium surface 162 defines the fly height 166 of the transducer 156, as previously discussed. The transducer 156 is illustrated having a sensor heater 168 in the proximity of a sensor 170, a writer heater 172 in the proximity of a writer 174 and sensor 170', and a reader heater 176 in the proximity of a reader 178 and a sensor 170". The sensors 170, 170' and 170", the writer 174, and the reader 178 are positioned at, or proximate to, the ABS 160. Activation of the thermally coupled heaters 168, 172, and 176 causes thermal actuation of corresponding sensors 170, 170' and 170" towards the magnetic storage medium 164, thereby reducing the distance (e.g., the fly height) therebetween.

Thermal asperity contact occurring at the contact points 182, 182' and 182" can be detected by a detector or other component coupled to the thermally actuated sensors 170, 170' and 170" and the location of the contact event can be recorded. The transducer 156 can be repositioned to similarly identify and record other locations of thermal asperity contact. In this manner, the topography of the surface 162 of the magnetic storage medium 164 can be mapped by repeatedly repositioning the transducer 156, actuating the heat source (e.g. by heaters 168, 172, and 174) corresponding the sensors 170, 170' and 170", detecting thermal asperity contact events, and recording the location thereof. Thereafter, the sensor heater 168 can be rendered electrically inoperable, and the one or more sensors 170 (optionally), 170' and 170" can be further used to detect head-medium contact during read/write operations. In some embodiments, the sensor 170 associated with the inoperable sensor heater 168 can be invalidated (e.g., ignored) for future use.

According to various embodiments, the sensor 170 and the dedicated sensor heater 168 are operated during a topographic evaluation of the magnetic recording medium 164, such evaluation often being performed prior to in-service use of the medium 164. The sensor heater 168 can be considered dedicated to the sensor 170, in that the sensor heater 168 is operable for a limited time for thermally actuating the sensor 170 (e.g., during the manufacturing phase). Upon expiration of this limited time, the sensor heater 168 is rendered inoperable. During manufacturing, for example, the sensor 170 is thermally actuated by the sensor heater 168 to perform a topographic evaluation of the magnetic recording medium 164, including detecting thermal asperities, voids, and other defective locations of the medium 164.

Use of a dedicated sensor heater 168 and sensor 170 allows the writer 174 and reader 178 to remain inactive during topographic evaluation of the medium 164. As such, the writer 174 and the reader 178 will be in a retracted state (e.g., retracted position) relative to the sensor 170. In other words, the sensor 170 will be relatively closer to the magnetic storage medium 164, and the writer 174 and the reader 178 will be relatively farther away from the magnetic storage medium 164. Such positioning of the writer 174 and the reader 178 father away from the magnetic storage medium 164 reduces the risk of damaging these sensitive components of the transducer. In some embodiments, the sensor heater 168 is no longer needed after completion of the topographical evaluation, and can be configured to be rendered functionally inoperable. The sensor 170 can, in certain embodiments, remain operable after rendering the sensor heater 168 inoperable, and be used for contact and/or fly height detection during the service life of the system. In some embodiments, both the sensor heater 168 and the sensor 170 can be rendered functionally inoperable after completion of a topographic evaluation of the magnetic recording medium 164.

During in-service use of the magnetic recording medium 164, actuation of the writer heater 172 will thermally actuate the writer 174 and cause the proximally located sensor 170' to move towards the magnetic storage medium 164. Additionally, or in the alternative, actuation of the reader heater 176 will thermally actuate the reader 178 and cause the proximally located sensor 170" to move towards the magnetic storage medium 164. The thermally actuated sensor 170' and/or 170" can be used for detecting head-medium contact at the writer 174 and/or at the reader 178 during write and/or read operations.

In some embodiments, the sensor heater 168 can be rendered inoperable upon receiving a predetermined signal. For example, in some embodiments, the electrical current flowing through the sensor heater 168 can be increased such that the thermal energy generated at the sensor heater 168 essentially "burns" the resistive heating element of the heater 168 and creates an electrically "open" branch at the heater. In other words, the electrical current flowing through the sensor heater 168 can be increased such that the electrical power dissipated at the sensor heater 168 will essentially "blow" the resistive element 168 like an electrical fuse, so as to create an electrically "open" branch at the heater 168. In a non-limiting representative embodiment, this can be accomplished without the need for additional bonding pads by electrically coupling the dedicated sensor heater 168 to the one or more bond pads used for the writer and reader heaters 174 and 178.

Figure 4:
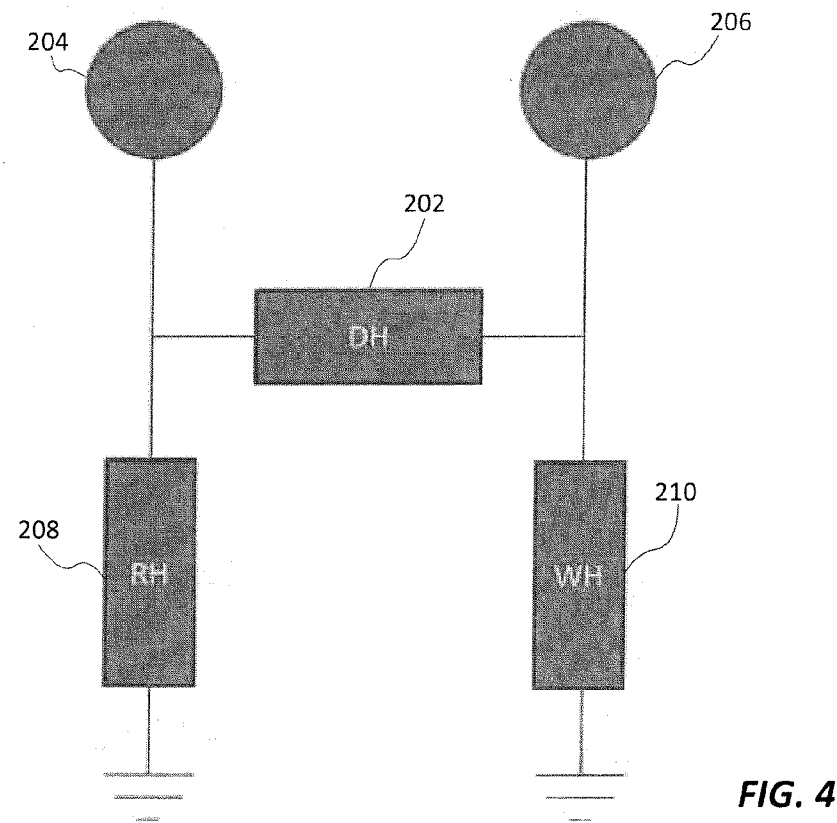
FIG. 4 illustrates an embodiment of a sensor heater electrically coupled to a reader heater and a writer heater.

FIG. 4 illustrates an embodiment of a sensor heater 202 electrically coupled to the electrical bonding pads 204 and 206 of a recording transducer respectively provided for the reader heater 208 and the writer heater 210. As such, the bonding pads 204 and 206 can be biased to alter the ratio of the electrical current flowing through the resistor of the respective heaters 202, 208 and 210. In some embodiments, a more pronounced thermal actuation of the sensor, relative to the thermal actuation of the reader/writer, can be achieved by applying opposing electrical potential of equal magnitude to the bonding pads 204 and 206. If the heaters 202, 208 and 210 have substantially similar electrical resistance, then one-half of the circuit current will flow through the sensor heater 202, and the remaining half will be equally divided between the reader and writer heaters 208 and 210. Accordingly, the electrical power dissipated in the sensor heater 202 will be four times greater than the electrical power dissipated in either of the reader and writer heaters 208 and 210. As will be apparent to one skilled in the art, the resistance of the heaters can be tuned to control the thermal energy generated in the heaters 202, 208 and 210. In certain embodiments wherein the heaters 202, 208 and 210 have substantially similar resistances, the thermal energy generated in the heaters 202, 208 and 210 can be controlled by manipulating the amount of electrical current flowing through each heater 202, 208 and 210.

Figure 5:
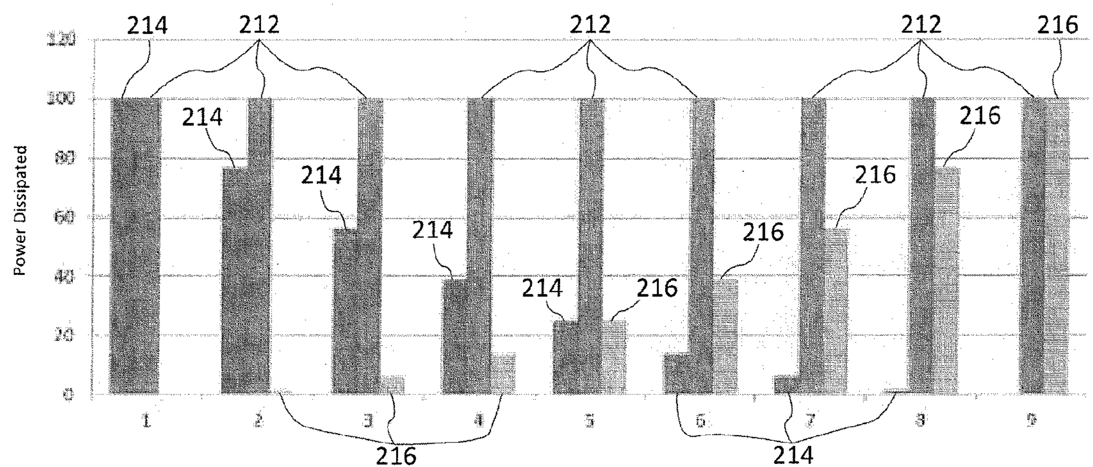
FIG. 5 illustrates the relative electrical power dissipated in the heaters of a transducer under varying biasing conditions in accordance with various embodiments.

FIG. 5 illustrates the relative electrical power dissipated in the representative heaters 202, 208 and 210 having equivalent resistance, wherein the same electrical potential difference is maintained between the bonding pads 204 and 206 and the absolute bias values on each pad 204 and 206 are varied between ground and full bias. The relative electrical power dissipated in the sensor heater 202 is depicted by the numeral 212, relative electrical power dissipated in the reader heater 208 is depicted by the numeral 214, and the relative electrical power dissipated in the writer heater 210 is depicted by the numeral 216.

As described elsewhere, the sensor heater 202 can be designed such that the electrical power dissipated, and the thermal energy generated, at the sensor heater 202 is greater than the electrical power dissipated, and the thermal energy generated, at the reader and the writer heaters 208 and 210. Accordingly, a sensor thermally actuated by the sensor heater 202 moves towards the magnetic storage medium to a greater extent than a reader and writer thermally actuated by the reader and the writer heaters 208 and 210. Therefore, the distance between the sensor and the magnetic storage medium will be smaller than that between the magnetic storage medium and each of the reader and the writer. As such, the reader and the writer will be in a retracted state (e.g., retracted position) relative to the sensor, and will be protected from harm during the topographical mapping operation.

Figure 6:
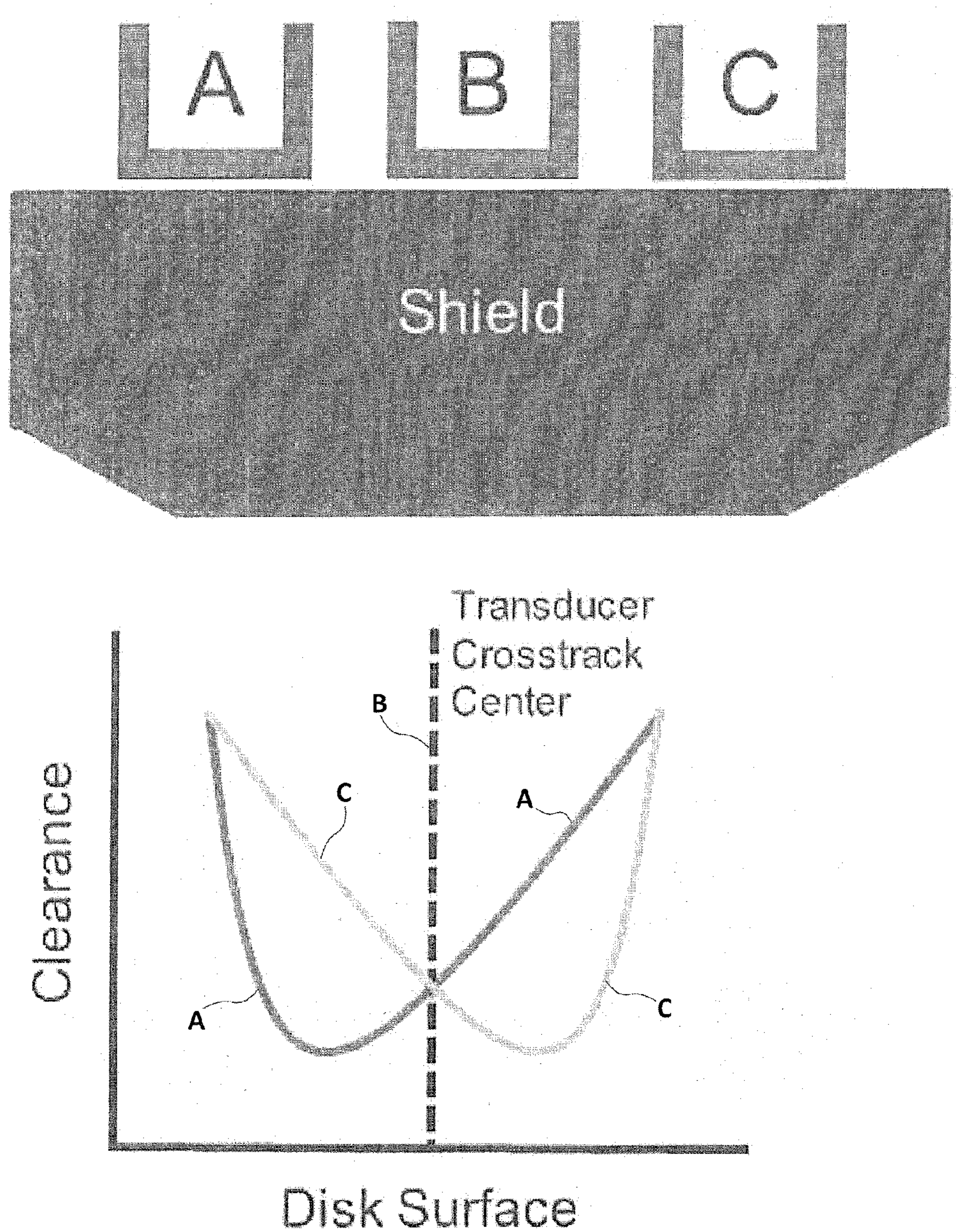
FIG. 6 illustrates representative locations for a sensor heater and a corresponding sensor in accordance with various embodiments, the sensor configured to at least sense thermal asperities of a magnetic storage medium.

In some embodiments, the reader and the writer can be protected during the topographical mapping operation by positioning the sensor heater and the sensor in a crosstrack or downtrack position on the transducer. In certain embodiments, the "electrically removable" sensor heater 202 can be placed anywhere in the crosstrack or downtrack direction of the transducer's ABS such that the closepoint of the sensor is at a location distant from any undesirable locations and/or fragile features of the transducer (e.g., the read and write poles). FIG. 6 illustrates some non-limiting representative locations for the sensor heater and the corresponding sensor. In some embodiments, during the topographical mapping operations, the closepoint of the sensor can be moved off the center track (e.g., in the crosstrack direction) by placing the electrically removable sensor heater 202 and the corresponding sensor towards the edges of the transducer's shields as illustrated by protrusions A and C in FIG. 6. In certain embodiments, for detecting asperities, the closepoint can be moved away from either the reader or the writer but the sensor is retained on the center track as illustrated by protrusion B in FIG. 6.

Figure 7:
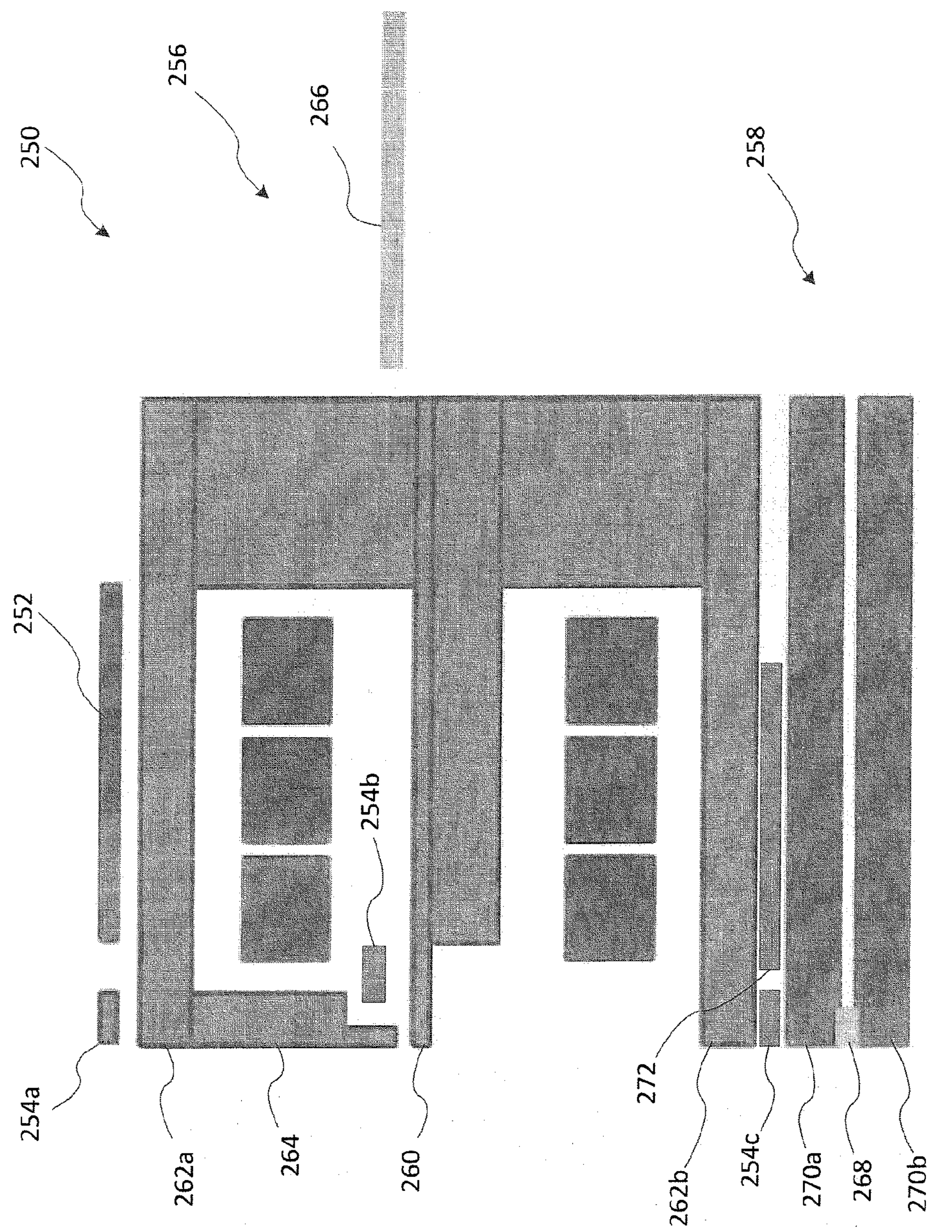
FIG. 7 illustrates representative locations for a multiplicity of sensors and a sensor heater relative to a reader and a writer in accordance with various embodiments, the sensor configured to at least sense thermal asperities of a magnetic storage medium.

It should be clearly understood that FIGS. 2 and 3 illustrate non-limiting representative locations and/or relative positioning of the sensor heater and the sensors 170, 170' and 170". FIG. 7 is a partial illustration of a transducer 250 showing representative locations for a sensor heater 252 and a multiplicity of sensors **254*a*-254*c* relative to a simplistically illustrated writer 256 and a simplistically illustrated reader 258. The writer 256 includes a write pole 260, write return poles 262*a* and 262*b*, forward shield 264 and writer heater 266. In some embodiments, the transducer 250 can include two or more writer heaters. The reader 258 includes a read pole 268, reader shields 270*a* and 270*b* and reader heater 272. In the embodiment illustrated in FIG. 7, the sensor heater 252 is shown isolated from the writer heater 266 and from the reader heater 272. The sensor heater 252 is illustrated in close proximity of the corresponding sensor 254*a*; and the sensors 254*a* and 254*b* are illustrated in close proximity of writer return pole 262*a* and the write pole 260, respectively. As described elsewhere, when sensor heater 252 is actuated, the closepoint will be defined by the sensor 254*a* corresponding to the actuated heater 252, and the reader 258 and the writer 256 will be in a retracted state away from the magnetic storage medium at a distance greater than the closepoint of the sensor 254*a*. As such, the reader 258 and the writer 256 can be protected from harm while the thermally actuated sensor 254*a* is used for detecting asperities when mapping the topography of a surface of a magnetic storage medium. Thereafter, according to some embodiments, the sensor heater 252 can be rendered inoperable, and one or both sensors 254*a* and 254*b* can be used to detect head-medium contact during the write operation when the writer heater 266 is actuated. Similarly, the sensor 254*c* can be used to detect head-medium contact during the read operation when the reader heater 272** is actuated.

As has been described, it is generally desirable to ensure that the one or more sensors, and not the reader and the writer poles, are closest to the magnetic storage medium during the topographical mapping operation. In other words, during the topographical mapping operation, the closepoints for the reader and the writer should be retracted away from the surface of the magnetic storage medium relative to the closepoints of the sensors. If the closepoints of the reader and the writer are not retracted, then transducer burnish and damage to the reader and writer can occur during the topographical mapping operation.

Figure 8:
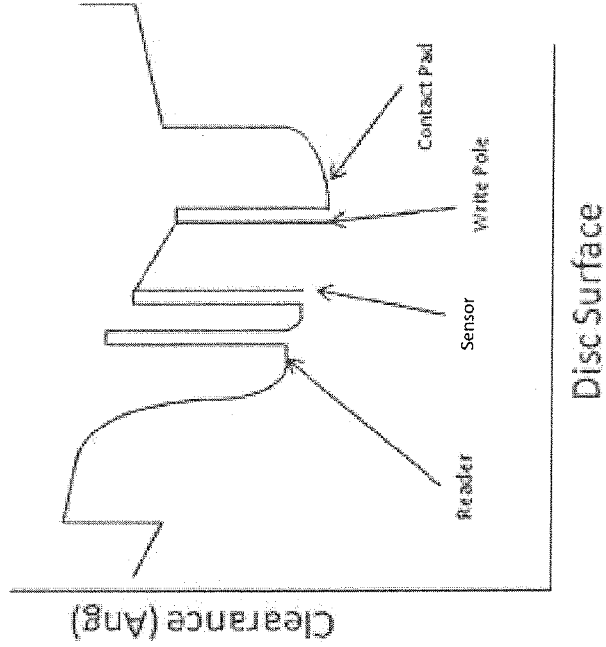
FIG. 8 illustrates a representative location for a sensor relative to a write pole and a contact pad in accordance with various embodiments, the sensor configured to at least sense thermal asperities of a magnetic storage medium.

In some embodiments, the transducer includes one, two or more than the two heaters that are thermally coupled to the transducer. The one or more heaters are used for ensuring that the write pole is at the closest point to the surface of the magnetic storage medium (writer closepoint) during write operations, and that the read pole (e.g., read sensor) is at the closest point to the surface of the magnetic storage medium (reader closepoint) during read operations. A sensor can be placed on the transducer only at a location at or near the ABS where the sensor does not interfere with or disrupt read/write operations. For detecting head-medium contact during the write operations, when the writer is the component closest to the magnetic storage medium, it is ideal or desirable to place a sensor between the write pole and a corresponding magnetic pad as illustrated in FIG. 8. However, such placement of the sensor will interfere with, and negatively impact, write operations. Therefore, the sensor should be located away from the write pole and the associated contact pads (e.g., the writer's upper and lower return poles). Consequently, the sensor closepoint will be at a location remote from the writer closepoint. While such placement of the sensor at a location remote from the writer can help protect the writer from damage when the sensor is used for detecting asperities during the topographical mapping operation, the sensor cannot be appropriately used for detecting head-medium contact during the write operation because the writer, not the sensor, will be closer to the magnetic storage medium.

Figure 9A:
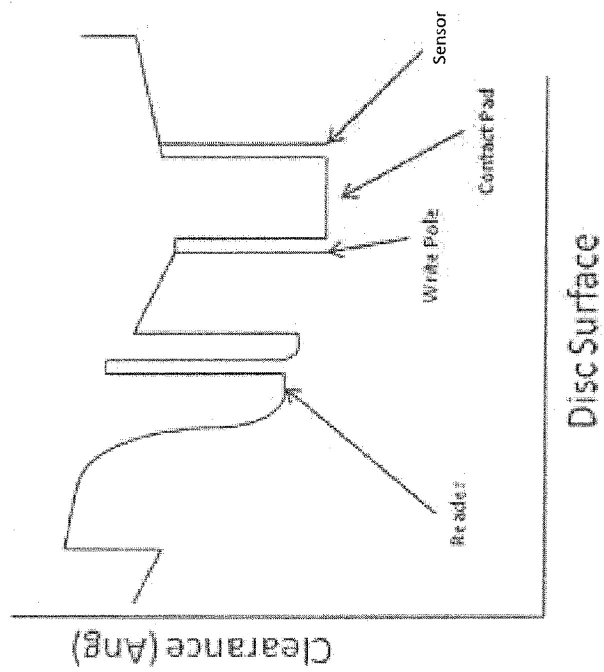
FIG. 9A illustrates another representative location for a sensor relative to a writer and a reader in accordance with various embodiments, the sensor configured to at least sense thermal asperities of a magnetic storage medium.

FIG. 9A is an illustration that shows how a sensor above a contact pad can be driven into contact much like a write pole. By knowing how fast the sensor approaches the disk surface by being driven by its own heater, the distance between the sensor and the disk surface can be inferred relative to the write pole at any fly height. The contact pad above the write pole provides additional heat transfer to the sensor when the closepoint is set to be on the write pole itself. Making the write pole, contact pad, and sensor have equivalent proximity to the disk surface can aid in heat transfer to the write pole and guarantee that the clearance setting will be accurate.

Figure 9B:
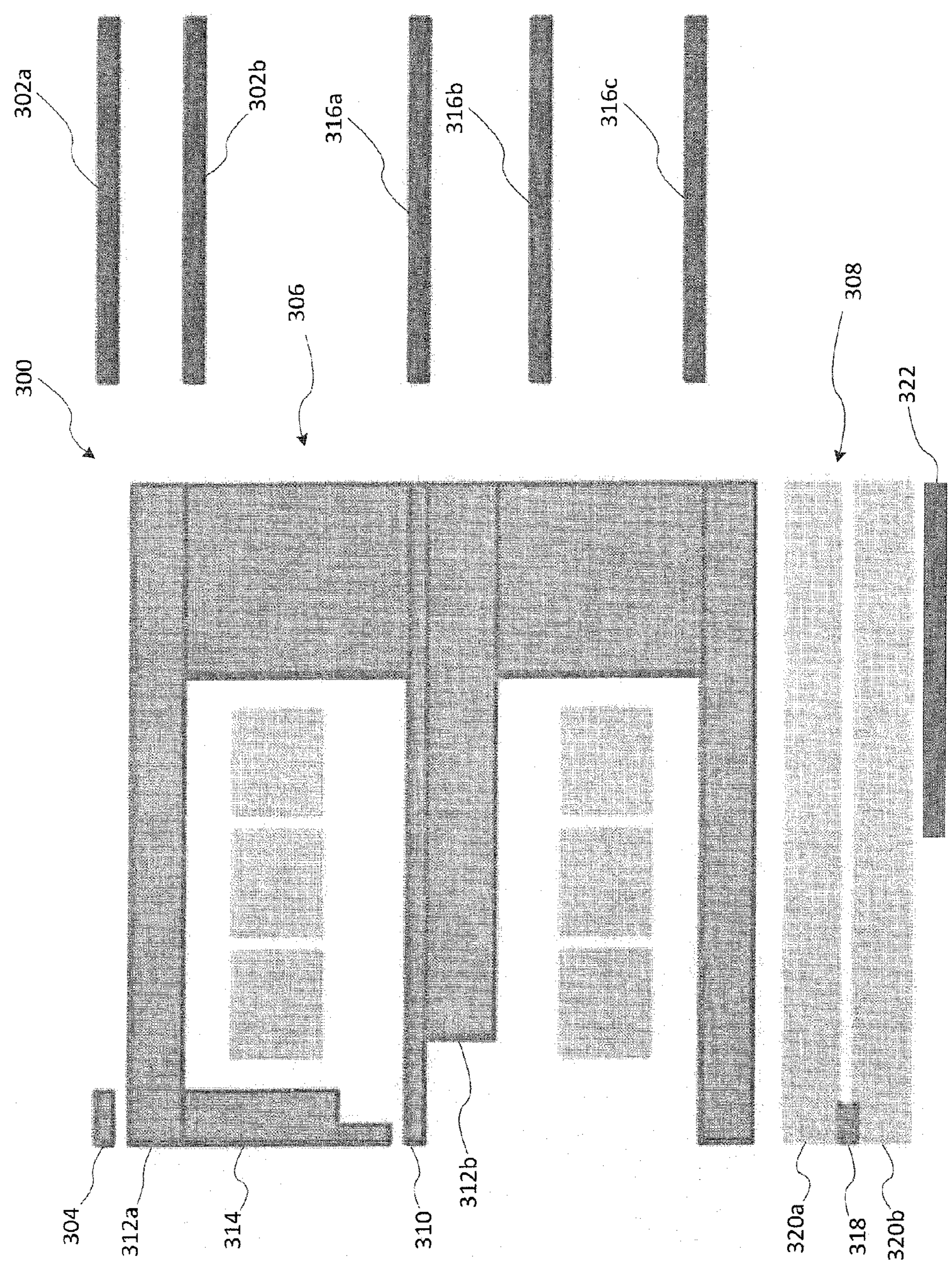
FIG. 9B is another view of the representative location illustrated in FIG. 9A.

FIG. 9B shows the relative heater positions that can drive different write pole-to-sensor distances to the disk surface. Heaters such as heaters **316*a*, 316*b* & 316*c*, for example, would favor to keeping the sensor further away from the disk surface as the write pole touches down. Heaters 302*a* & 302*b* can be driven to make sure that the sensor is either equivalent to the write pole or even ahead of the write pole (such as heater 302*a*) towards to the disk surface. To be electrically removable, it may be favorable to keep heaters 302*b*, 316*a-c* active and to use heater 302*a* as a removable heater. Driving with heater 302*a*** would allow the sensor to contact the disk surface first and be more usable for thermal asperity detection. This would provide more protection to the read and write elements since they would be further from the disk surface and out of harms way.

FIGS. 9A and 9B, according to various embodiments, illustrate a transducer 300 having a sensor that can be used for detecting asperities during a topographical mapping operation. Transducer 300 is illustrated having sensor heaters **302*a* and 302*b*, a sensor 304, a writer 306, and a reader 308. The writer 306 is illustrated having a write pole 310, writer upper return pole 312*a* (e.g., serving as a contact pad), writer lower return pole 312*b*, forward shield 314 and writer lower heaters 316*a*-316*c*. For completeness, the reader 308 is illustrated having a read pole 318, reader shields 320*a* and 320*b* and reader heater 322**.

It should be noted that it is not always necessary to provide two sensor heaters 302*a* and 302*b*. In some embodiments, the transducer 300 can include one, two or more than two sensor heaters. Also, it is not always necessary to provide three writer lower heaters 316*a*-316*c*. In some embodiments, the transducer 300 can include one, two, three or more than three writer lower heaters. In certain embodiments, the one or more sensor heaters 302*a*/302*b* (and/or one or more writer lower heaters 316*a*/316*b*/316*c*) are placed in the proximity of the sensor 304. In some embodiments, the one or more sensor heaters are controlled independently of any other transducer heaters (e.g., reader and/or writer heaters). In certain embodiments, the one or more sensor heaters are electrically coupled in series with a corresponding writer upper heater and/or a reader heater. Of course, the heaters are all thermally coupled to the transducer 300.

FIG. 9B illustrates relative positioning of the one or more sensor heaters 302*a*/302*b* and the one or more writer lower heaters 316*a*/316*b*/316*c* configured for extending the sensor 304 and the writer pole 310 towards or away from the magnetic storage medium. Activating only the one or more writer lower heaters 316*a*/316*b*/316*c* will extend the writer pole 310 towards the magnetic storage medium while retaining the sensor 304 in a retracted position. Activating only the one or more sensor heaters 302*a*/302*b* will extend the sensor 304 towards the magnetic storage medium while retaining the writer pole 310 in a retracted position. Concurrent activation of the one or more sensor heaters 302*a*/302*b* and the one or more writer lower heaters 316*a*/316*b*/316*c* will extend both the sensor 304 and the writer pole 310 towards the magnetic storage medium. Concurrently manipulating the thermal energy generated by the heaters will determine whether the sensor 304 or the writer pole 310 will be closer to the magnetic storage medium. For instance, if the thermal energy proximate the sensor 304 is greater than that at the writer pole 310, then the sensor 304, rather than the writer pole 310, will be closer to the magnetic storage medium. Similarly, the writer pole 310, rather than the sensor 304, will be closer to the magnetic storage medium if the thermal energy proximate the writer pole 310 is greater than that at the sensor 304. Thus, the sensor 304 and the writer pole 310 can be made coplanar and approximately equidistant from the magnetic storage medium by manipulating the thermal energy generated by the individual heaters 302*a*/302*b* and 316*a*/316*b*/316*c*.

In some embodiments, only the sensor heater 302*a* is activated for extending the sensor 304 towards the magnetic storage medium for the purpose of detecting thermal asperities while retaining the writer pole 310 and the read pole 318 in a retracted (e.g., protected) position away from the magnetic storage medium. After the topographical mapping of the magnetic storage medium has been completed, the sensor heater 302*a* can be electrically removed (e.g., electrically deactivated). Thereafter, the sensor heater 302*b* and the one or more writer lower heaters 316*a*/316*b*/316*c* can be activated to extend the sensor 304 and the writer pole 310 towards the magnetic storage medium. As described, the thermal energy at the sensor 304 and at the writer pole 310 can be manipulated to adjust the relative positioning of the sensor 304 and the writer pole 310.

It should be apparent that if the one or more writer lower heaters 316*a*/316*b*/316*c* are not actuated concurrently with the one or more sensor heaters 302*a*/302*b*, then the write pole 310 (e.g., the writer closepoint) will be in a retracted position such that the sensor 304 will be closer to the magnetic storage medium than the write pole 310. As such, the write pole 310 can be protected from damage while the sensor 304 is used during the topological mapping operation. If the one or more sensor heaters 302*a*/302*b* are not actuated concurrently with the one or more writer lower heaters 316*a*/316*b*/316*c*, then the write pole 310 will be closer to the magnetic storage medium than the sensor 304. If the transducer 300 is operated in this manner, the probability of damaging the writer increases.

It should now be apparent that the distance between the magnetic storage medium and both the sensor 304 and the write pole 310 can be adjusted (e.g., controlled) by manipulating the thermal energy generated (e.g., the electrical power dissipated) in both the one or more sensor heaters 302*a*/302*b* and the one or more writer lower heaters 316*a*/316*b*/316*c*. In some embodiments, the one or more writer upper heaters (or sensor heaters) 302*a*/302*b* and the one or more writer lower heaters 316*a*/316*b*/316*c* can be actuated in series or in parallel such that both the sensor 304 and the write pole 310 can be concurrently extended towards the magnetic storage medium. The closepoints for both the sensor 304 and the writer pole 310 can be made coplanar with the writer upper return pole (or contact pad) 312*a* such that the sensor 304 can also be used for detecting head-medium contact during the write operation. In certain embodiments, the one or more sensor heaters (or writer upper heaters) 302*a*/302*b* and the one or more writer lower heaters 316*a*/316*b*/316*c* can be actuated independently of each other for independently positioning the sensor closepoint and the writer closepoint as necessary during the write operation.

FIGS. 9A and 9B illustrate an embodiment wherein the sensor 304 is proximate the trailing edge of the transducer 300 and the writer upper return pole (e.g., the contact pad) 312*a* is between the sensor 304 and the writer pole 310. In other words, in the direction from the trailing edge to the leading edge, the transducer 300 includes the sensor 304, the writer upper return pole (e.g., the contact pad) 312*a*, and the writer pole 310. As such, the contact pad (e.g., writer upper return pole 312*a*) serves as an electrical shield for shielding the sensor 304 from the writer pole 310.

In some embodiments, if the positional relationship between the sensor 304 and the write pole 310 is known, then knowledge of the sensor closepoint can be used to infer the writer closepoint. For instance, when the one or more writer lower heaters 316*a*/316*b*/316*c* are actuated to define the closepoint as between the writer pole 310 and the magnetic storage medium, heat is transferred through the contact pad 312*a* to the sensor 304. By activating the one or more sensor heaters 302*a*/302*b* concurrently with the one or more writer lower heaters 316*a*/316*b*/316*c*, the sensor 304, the writer pole 310 and the contact pad 312*a* can be made coplanar by manipulating the heaters to equilibrate the heat transfer through the contact pad 312*a*. Thus, if the rate at which the sensor 304 extends towards the magnetic storage medium, in response to activation of the one or more sensor heaters 302*a*/302*b*, is known, then the distance between the sensor 304 and the magnetic storage medium, relative to the writer pole 310 at any fly height, can be determined. This distance between the sensor 304 and the magnetic storage medium is an indication of the distance between the writer pole 310 and the magnetic storage medium because the sensor 304, the writer pole 310, and the contact pad 312*a* are coplanar.

It should be apparent that if the reader heater 322 is not actuated concurrently with the one or more sensor heaters 302*a*/302*b*, then the read pole (e.g. the reader closepoint) will be in a retracted position such that the sensor 304 will be closer to the magnetic storage medium than the read pole 318. As such, read pole 318 can be protected from damage while the sensor 304 is used during the topological mapping operation.

If the one or more sensor heaters 302a/302b are not actuated concurrently with the reader heater 322, then the read pole 318 will be closer to the magnetic storage medium than the sensor 304. If the transducer 300 is operated in this manner, the probability of damaging the reader increases.

It should now be apparent that the distance between the magnetic storage medium and both the sensor 304 and the read pole 318 can be adjusted (e.g., controlled) by manipulating the thermal energy generated (e.g., the electrical power dissipated) in both the one or more sensor heaters 302a/302b and the reader heater 322. In some embodiments, the one or more writer upper heaters (or sensor heaters) 302a/302b and the reader heater 322 can be actuated in series or in parallel such that both the sensor 304 and the read pole 318 can be concurrently extended towards the magnetic storage medium. By manipulating the thermal energy generated by one or more sensor heaters and the reader heater 322, the closepoints for both the sensor 304 and the read pole 318 can be made coplanar such that the sensor 304 can also be used for detecting head-medium contact during the read operation. In certain embodiments, the one or more sensor heaters (or writer upper heaters) 302a/302b and the reader heater 322 can be actuated independently of each other for independently positioning the sensor closepoint and the reader closepoint as necessary during the read operation.

In the foregoing, while the sensor 304 used in conjunction with the read pole 318 is illustrated and described as located proximate the writer upper pole 312a, this is not necessary always the case. In some embodiments, a separate or additional sensor may be provided proximate the read pole 318. This additional sensor, for example sensor 254c in FIG. 7, can then be used to detect head-medium contact during the read operation by thermal actuation of both the sensor and the reader by the reader heater. In certain embodiments, the sensor proximate the read pole may include a sensor heater for thermally actuating the sensor for detecting asperity contact during the topographical mapping operation. The sensor heater can then be rendered inoperable after the mapping operating has been completed.

From the foregoing, it should be apparent that, in some embodiments, it is possible to concurrently extend the sensor 304, the write pole 310, the read pole 318 and, if provided, the sensor proximate the read pole 318 towards the magnetic storage medium by concurrently actuating the one or more sensor heaters (or writer upper heaters) 302a/302b, the one or more writer lower heaters 316a/316b/316c and the reader heater 322. Accordingly, the sensor 304 can be used to detect head-medium contact during the write operation and the sensor proximate the read pole 318, if provided, can be used to detect head-medium contact during the read operation. In embodiments having more than one sensor, selected sensors can be used for detecting head-medium contact during both write and read operations.

Figure 10:
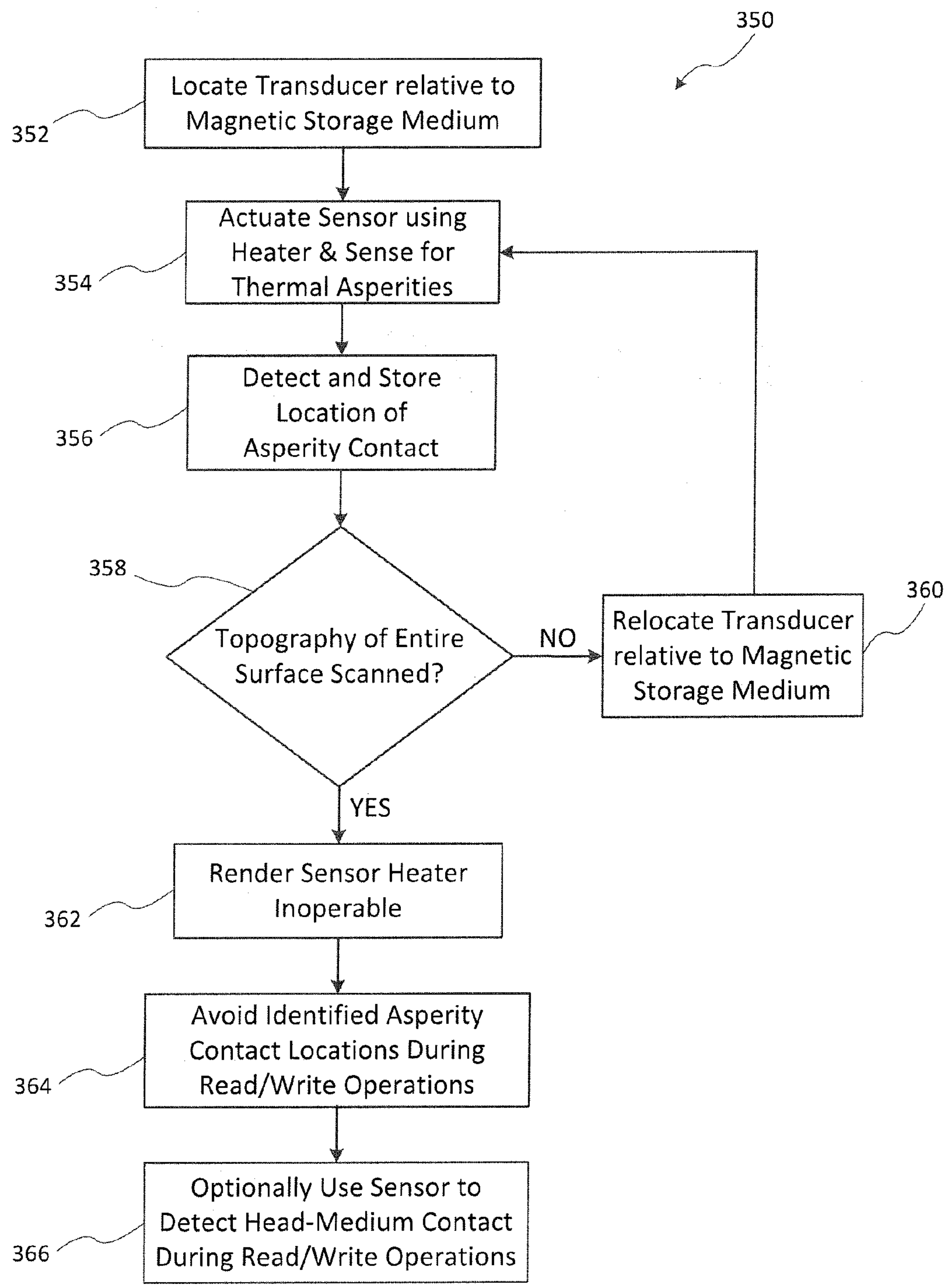
FIG. 10 illustrates a method of mapping the topography of a magnetic storage medium with a sensor in accordance with various embodiments, the sensor configured to at least sense thermal asperities of a magnetic storage medium.

FIG. 10 is a flowchart for an embodiment of a method 350 of using a thermally actuated sensor to detect thermal asperities during a topographical mapping operation. As illustrated, the transducer is located relative to the magnetic storage medium 352, and a sensor is actuated 354 using a sensor heater. The sensor is used to sense for thermal asperities or other surface abnormalities of the magnetic storage medium, and the locations thereof are recorded (e.g., stored) 356. A check is performed to determine if the topographical mapping of the entire surface of the magnetic storage medium has been completed 358. If the mapping has not been completed, then the transducer is relocated relative to the magnetic storage medium 360, and the sensor is used 354 for detecting and storing the location of asperity contact 356 at the position where the transducer is located. These steps of relocating the transducer relative to the magnetic storage medium 360, actuating the sensor heater 354, and detecting and storing the location of asperity contact 356 are repeated until it is determined 358 that the entire or desired portion of the surface of the magnetic storage medium has been topographically mapped for asperities, voids, abnormalities, etc., and their locations recorded. The sensor heater can then be rendered inoperative 362. Then, the information from the topographical mapping is used 364 to avoid writing and/or reading data at the locations whereat asperities, voids, abnormalities, etc., exist on the surface of the magnetic storage medium. Thereafter, the sensor can optionally be used to detect head-medium contact during read/write operations 366.

It is to be understood that even though numerous characteristics of various embodiments have been set forth in the foregoing description, together with details of the structure and function of various embodiments, this detailed description is illustrative only, and changes may be made in detail, especially in matters of structure and arrangements of parts illustrated by the various embodiments to the full extent indicated by the broad general meaning of the terms in which the appended claims are expressed.

What is claimed is:

1. An apparatus, comprising:

a transducer configured to interact with a magnetic storage medium;

a sensor at the transducer and configured to at least sense thermal asperities of the medium; and a sensor heater dedicated to thermally actuate the sensor, the sensor heater configured to be rendered inoperable in response to the sensor heater receiving a predetermined signal.

2. The apparatus of claim 1, wherein the transducer comprises:

a writer;

a reader;

at least one writer heater configured to thermally actuate the writer; and a reader heater configured to thermally actuate the reader.

3. The apparatus of claim 1, wherein the predetermined signal is a signal that creates an electrically open current path in the sensor heater.

4. The apparatus of claim 1, wherein:

the sensor is configured to be operable subsequent to the sensor heater becoming inoperable.

5. The apparatus of claim 1, wherein:

the sensor is configured to be rendered inoperable subsequent to the sensor heater becoming inoperable.

6. The apparatus of claim 1, wherein:

the transducer comprises a writer and a reader;

the sensor is situated away from the writer and the reader; and the sensor heater is configured to thermally actuate the sensor to define a close point of the transducer located away from close points respectively associated with the writer and the reader.

7. The apparatus of claim 1, wherein the sensor is configured to sense for one or both of thermal asperities and voids of the magnetic storage medium.

8. The apparatus of claim 1, wherein:
the transducer comprises a burnisher at or near an air bearing surface of the transducer; and
the burnisher is configured to be thermally actuated to reduce a size of thermal asperities of the magnetic storage medium with which it contacts.

9. The apparatus of claim 1, wherein:
the transducer further comprises a writer heater, a writer having a write pole, and a contact pad;
the sensor is adjacent the contact pad; and
the contact pad is between the sensor and the write pole.

10. The apparatus of claim 9, wherein:
the apparatus comprise a leading edge and a trailing edge; and
the sensor is closer to the trailing edge of the transducer than the contact pad.

11. The apparatus of claim 9, wherein the writer heater and the sensor heater are configured to operate cooperatively to modify a profile of the contact pad.

12. The apparatus of claim 9, wherein the writer comprises a writer return pole configured to serve as the contact pad.

13. The apparatus of claim 9, wherein the contact pad serves as an electrical shield for shielding the sensor from the writer.

14. The apparatus of claim 9, wherein:
the transducer further comprises a reader and a reader heater; and
the sensor heater, the writer heater, and the reader heater are configured to operate cooperatively to modify a location of a close point of the transducer.

15. The apparatus of claim 1, wherein the sensor is configured to sense contact between the transducer and the magnetic storage medium.

16. An apparatus, comprising:
a writer, a reader, and a sensor configured to at least sense thermal asperities of a magnetic storage medium;
a writer heater configured to thermally actuate the writer;
a reader heater configured to thermally actuate the reader; and
a sensor heater configured to thermally actuate the sensor and electrically coupled between the writer and reader heaters, the sensor heater configured to receive a current load greater than that of the writer and reader heaters and to be rendered inoperable in response to the sensor heater receiving a predetermined signal while the writer and reader heaters remain operable.

17. A method, comprising:
thermally actuating a sensor of a slider using a sensor heater;
scanning a magnetic storage medium for thermal asperities using the thermally actuated sensor;
rendering the sensor heater inoperable in response to the sensor heater receiving a predetermined signal; and
sensing for contact between the slider and one or both of thermal asperities and the magnetic storage medium using the sensor subsequent to rending the sensor heater inoperable.

18. The apparatus of claim 16, wherein the predetermined signal is a signal that creates an electrically open current path in the sensor heater.

19. The apparatus of claim 16, wherein the sensor is configured to be operable subsequent to the sensor heater becoming inoperable.

20. The apparatus of claim 16, wherein the sensor is configured to be rendered inoperable subsequent to the sensor heater becoming inoperable.

21. The apparatus of claim 16, wherein the sensor heater is configured to thermally actuate the sensor to define a close point of the transducer located away from close points respectively associated with the writer and the reader.

* * * * *